US00PP32923P2

(12) United States Plant Patent
Kordes

(10) Patent No.: US PP32,923 P2
(45) Date of Patent: Mar. 30, 2021

(54) MINIATURE ROSE PLANT NAMED 'KORPOT090'

(50) Latin Name: *Rosa hybrida*
Varietal Denomination: KORpot090

(71) Applicant: W. KORDES' SÖHNE Rosenschulen GmbH & Co KG, Offenseth-Sparrieshoop (DE)

(72) Inventor: Wilhelm-Alexander Kordes, Klein Offenseth-Sparrieshoop (DE)

(73) Assignee: W. KORDES' SÖHNE ROSENSCHULEN GMBH & CO. KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 16/602,927

(22) Filed: Dec. 30, 2019

(51) Int. Cl.
*A01H 5/02* (2018.01)
*A01H 6/74* (2018.01)

(52) U.S. Cl.
USPC ..... Plt./116
CPC ..... *A01H 6/749* (2018.05)

(58) Field of Classification Search
USPC ..... Plt./116
CPC ..... A01H 6/749
See application file for complete search history.

(56) References Cited

U.S. PATENT DOCUMENTS

PP18,840 P2 5/2008 Kordes
PP30,573 P2 6/2019 Kordes

OTHER PUBLICATIONS

UPOV hit on Plant Breeders' Right QZ PBR 20192706, filed Oct. 23, 2019 to a rose plant named, 'KORpot090'.*

* cited by examiner

*Primary Examiner* — Anne Marie Grunberg
(74) *Attorney, Agent, or Firm* — Panitch Schwarze Belisario & Nadel LLP; Stephany G. Small; Travis W. Bliss

(57) ABSTRACT

A new and distinct variety of miniature rose plant, herein referred to by its cultivar name, 'KORpot090', is provided which forms abundantly on a substantially continuous basis attractive, red and white colored blossoms. Attractive vigorous vegetative is formed, which contrasts beautifully with the blossoms. The growth habit is compact. The new variety is well suited for providing attractive ornamentation in the landscape.

1 Drawing Sheet

Botanical/commercial classification:
Latin name—*Rosa hybrida.*
Varietal denomination—'KORpot090'.

The new variety of *Rosa hybrida* Miniature Rose Plant of the present invention was created during 2014 at Offenseth-Sparrieshoop, Germany by artificial pollination wherein two parents were crossed which previously had been studied in the hope that they would contribute the desired characteristics. The female parent (i.e., seed parent) of the new variety was the 'KORpot054' variety (non-patented). The male parent (i.e., pollen parent) was an unnamed seedling from the cross ('KORpolare' x unnamed seedling). The 'KORpolare' variety is patented as U.S. Plant Pat. No. 18,840.

The parentage can be summarized as follows:

'KORpot054' x ('KORpolare' x unnamed seedling)

The seeds resulting from the above pollination were sown and small plants were obtained which were physically and biologically different from each other. Selective study resulted in the identification of a single plant of the new variety.

It was found that the new variety of rose plant of the present invention possesses the following combination of characteristics:

(a) forms attractive, red and white colored blossoms,
(b) displays a compact growth habit, and
(c) exhibits vigorous vegetation.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'KORpot054' variety (i.e., the seed parent) displays solid red colored flowers, whereas the new variety displays red and white colored flowers. In addition, the ('KORpolare' x unnamed seedling) variety (i.e., the pollen parent) displays solid red colored flowers, whereas the new variety displays red and white colored flowers and the male parent exhibits smaller flower size and a less bushy growth habit compared to the new variety. Moreover, the new variety can be readily distinguished from other similar non-parental varieties. For example, the 'KORpot084' variety (U.S. Plant Pat. No. 30,573) displays red and pink striped colored flowers, whereas the new variety displays red and white colored flowers, and the 'KORpot084' variety exhibits larger flowers and a slightly higher petal count than the new variety.

The new variety has been found to undergo asexual propagation in Klein Offenseth-Sparrieshoop, Germany by a number of routes, such as vegetative cuttings. Asexual propagation techniques in Germany, such as vegetative cuttings, have shown that the characteristics of the new variety are homogeneous, stable, and strictly transmissible by such asexual propagation from one generation to another. Accordingly, the new variety undergoes asexual propagation in a true-to-type manner.

The new variety has been named 'KORpot090'.

The first offer for sale was Jan. 1, 2019 by the inventor or another who obtained the new variety directly or indirectly from the inventor.

BRIEF DESCRIPTION OF THE PHOTOGRAPHS

The accompanying photograph shows, as nearly true as it is reasonably possible to make the same in color illustrations of this character, a typical specimen of the new variety. The illustrated rose plant of the new variety was approximately twelve weeks of age and was observed at Odense, Denmark while growing indoors on its own roots in 10.5 cm containers.

The drawing—illustrates a specimen of a plant displaying floral buds and flowers at varying points of opening.

DETAILED BOTANICAL DESCRIPTION

The chart used in the identification of colors is that of The Royal Horticultural Society (R.H.S. Colour Chart, 2015 edition). The terminology which precedes reference to the chart has been added to indicate the corresponding color in more common terms. The description is based on the observation of a one-year-old specimen of the new variety, observed during September, while growing in a one-gallon container on its own roots in a greenhouse in Cochranville, Pa.

Commercial classication: Miniature Rose Plant.

Plant:

*Habit*.—Compact and bushy.

*Height*.—Approximately 37.0 cm on average.

*Width*.—Approximately 35.0 cm on average.

Branches:

*Stem color*.—Commonly near Yellow-Green Group 144A.

*Length*.—Main stems: approximately 37.0 cm on average. Secondary stems: approximately 10.0 cm on average.

*Texture*.—Glabrous.

*Thorns*.—Young thorns: sparse amount; color is commonly near Greyed-Orange Group N167A; length is approximately 4.0 mm on average; and width is approximately 3.0 mm on average at point of attachment.

Foliage:

*Young and old foliage color*.—Upper surface: commonly near Green Group 137A with indistinguishable venation. Under surface: commonly near Green Group 137B with indistinguishable venation.

*Petiole*.—Upper and under surfaces: texture is smooth; color is commonly near Yellow-Green Group 144A. Length: approximately 2.5 cm on average. Width: approximately 2.0 mm on average.

*Rachis*.—Color: upper surface is commonly near Yellow-Green Group 144A, under surface is commonly near Green Group 143C.

*Stipules*.—Length: approximately 1.0 cm on average. Width: approximately 5.0 mm on average. Margin: entire to erose. Color: upper surface is commonly near Yellow-Green Group 144A, under surface is commonly near Yellow-Green Group 144B.

*5-leaflet leaf*.—Length: approximately 10.5 cm on average. Width: approximately 6.3 cm on average.

*Leaf margin*.—Serrate.

*Glossiness of upper side of leaf*.—Semi-glossy.

Leaflets:

*Number of leaflets*.—3, 5, and 7.

*Shape*.—Ovate; apex is acute; and base is rounded.

*Venation pattern*.—Reticulate.

*Texture*.—Upper and under surfaces is smooth.

*Terminal leaflet*.—Length: approximately 4.6 cm on average. Width: approximately 2.4 cm on average.

*Lower leaflet*.—Length: approximately 3.0 cm on average. Width: approximately 1.5 cm on average.

Inflorescence:

*Number of flowers*.—Generally about 10-12 blooms on average on a plant at once.

*Number of blooms per stem*.—Typically 1-4 blooms per stem on average.

*Peduncle*.—Length: approximately 4.0 cm on average. Diameter: approximately 3.0 mm on average. Surface texture: glabrous. Strength: strong. Color: commonly near Yellow-Green Group 144A.

*Sepals*.—Number: commonly 5. Length: approximately 2.5 cm on average. Width: approximately 7.0 mm on average. Margin: entire with occasional extensions on two or three sepals measuring approximately 7.0 mm in length on average and 3.0 mm in width on average. Upper surface color and texture: commonly near Yellow-Green Group 144A; covered in short pubescence. Under surface color and texture: commonly near Yellow-Green Group 144A; puberulent. Shape: lanceolate. Apex: acute to aristate. Base: truncate or flat as it joins the receptacle.

*Bud*.—Shape: globular to pointed. Length: approximately 2.0 cm on average. Width: approximately 1.1 cm on average. Color when opening: commonly near Red-Purple Group 60B.

*Flower*.—Diameter: approximately 4.0 cm on average. Height: approximately 1.5 cm on average. Duration: flower is on the plant approximately 20 days. Form: double, cuplike. Profile: flat. Number of petals under normal conditions: approximately 23 petals on average. Shape of the petal: overall: broadly obovate. apex: round. base: cuneate. Petal length: inner petals are approximately 1.6 cm on average; outer petals are approximately 2.0 cm on average. Petal width: inner petals are approximately 1.3 cm on average; outer petals are approximately 2.0 cm on average. Petal margin: entire. Petal drop: good. Petals reflex: one-by-one. Fragrance: none noticeable. Petal color when first and fully open: upper surface: commonly near Red Group N45A with ⅓ of the petal base near Yellow Group 8D. under surface: commonly near Red-Purple Group 63B and 63A at the margin with ⅓ of the petal base near Yellow Group 8D. Petal color when fading: upper surface: commonly near Red Group 53B with ⅓ of the petal base near White Group 155B. under surface: commonly more than ⅓ of petal base near White Group 155B transitioning to near Red Purple Group 63B and 63A at the margin. Petal texture: upper and lower surfaces are glabrous. Petaloids: typically 7 per flower; color of upper surface is commonly near Red Group 53A and near Yellow-Orange Group 16B at the base; under surface is commonly near Red-Purple Group 63A and near Yellow-Orange Group 16C at the base; length is approximately 1.5 cm on average; width is approximately 7.0 mm on average; texture is smooth; margin is variable, entire to erose; shape is variable, oblong and mostly curving inward; apex is round; base is cuneate.

*Receptacle*.—Color: commonly near Yellow-Green Group 144A. Diameter: approximately 6.0 mm on average. Surface texture: smooth. Shape: round.

*Stamen*.—Number is approximately 120 on average. Anthers: number is approximately 120 on average; color is commonly near Greyed-Purple Group 187A; length is approximately 2.5 mm on average; and shape is oval. Filaments: length is approximately 0.5 cm on average and color is commonly near Yellow Group 11B.

*Pistils*.—Arrangement is separate and free; number is approximately 55 on average. Styles: length is less than 6.0 mm on average and color is mostly near Red Group 42A and some exhibiting a small hint of near Yellow Group 11C at the base of the stigma. Stigmas: diameter is typically less than 1.0 mm; color is commonly near Greyed-Orange Group 177A; shape is fan shaped.

*Ovary*.—Color is commonly near White Group 155D; length is approximately 2.0 mm on average, and width is approximately 1.0 mm on average.

*Pollen*.—None observed.

*Hips*.—None observed.

Development:

*Vegetation*.—Dark green, vigorous and strong.

*Blooming*.—Abundant and reblooms well from a trim.

*Hardiness*.—Unknown.

*Resistance to disease*.—Good resistance to Botrytis (*Botrytis cinerea*) disease under normal greenhouse growing conditions in Cochranville, Pa.

Plants of the 'KORpot090' variety have not been observed under all possible environmental conditions to date. Accordingly, it is possible that the phenotypic expression may vary somewhat with changes in light intensity and duration, cultural practices, and other environmental conditions.

I claim:

1. A new and distinct Miniature Rose Plant characterized by the following combination of characteristics:

(a) forms attractive, red and white colored blossoms, (b) displays a compact growth habit, and (c) exhibits vigorous vegetation;

substantially as herein shown and described.

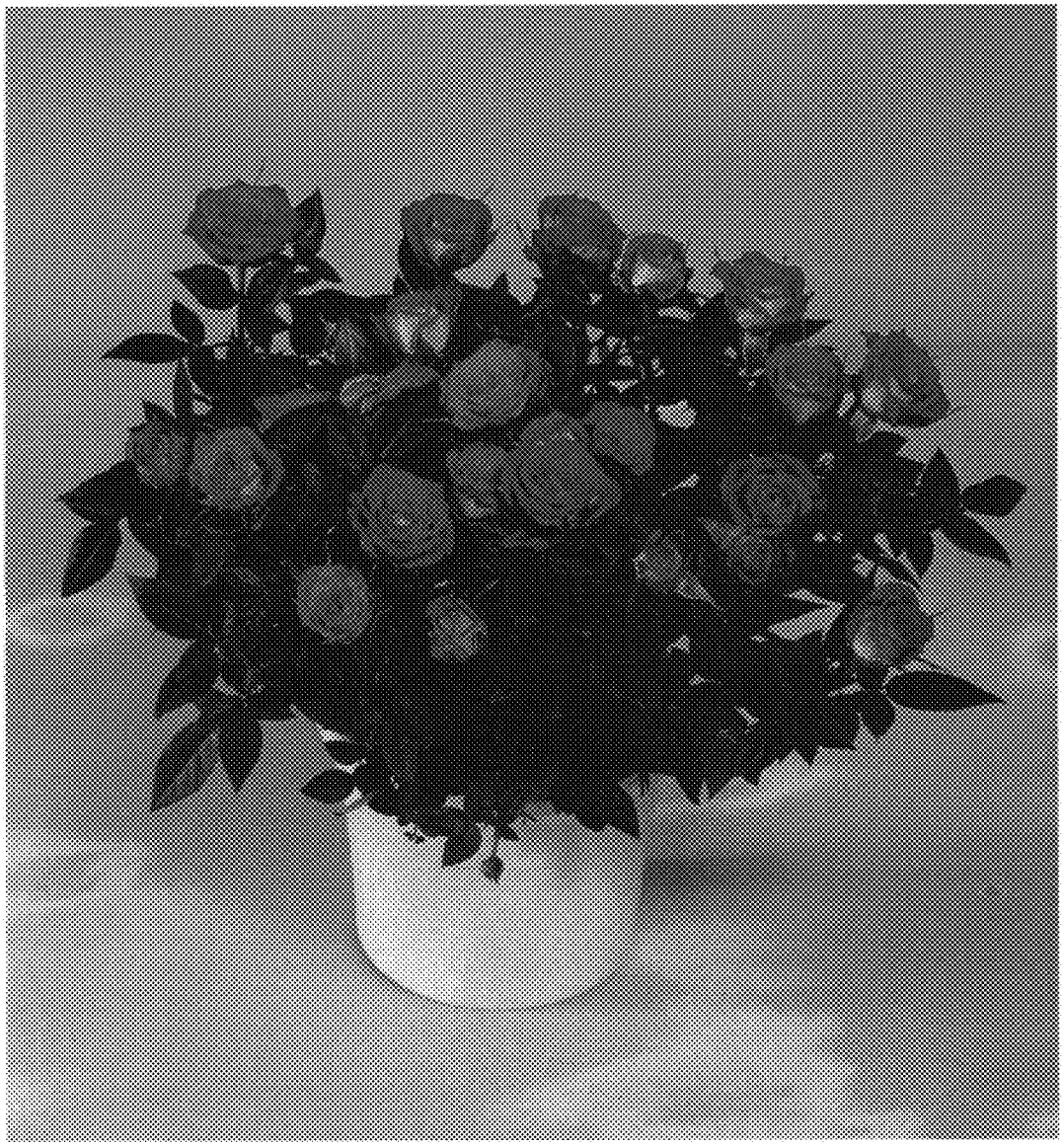

* * * * *